(12) United States Patent
Yang et al.

(10) Patent No.: US 11,759,158 B2
(45) Date of Patent: Sep. 19, 2023

(54) SYSTEMS AND METHODS FOR CONTROLLING IMAGING DEVICE

(71) Applicant: SHANGHAI UNITED IMAGING HEALTHCARE CO., LTD., Shanghai (CN)

(72) Inventors: Jia Yang, Shanghai (CN); Yongqin Xiao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 297 days.

(21) Appl. No.: 17/172,097

(22) Filed: Feb. 10, 2021

(65) Prior Publication Data
US 2021/0196218 A1 Jul. 1, 2021

Related U.S. Application Data

(63) Continuation of application No. PCT/CN2019/102349, filed on Aug. 23, 2019.

(30) Foreign Application Priority Data

Aug. 23, 2018 (CN) .......................... 201810966308.X
Sep. 21, 2018 (CN) .......................... 201811109281.9

(51) Int. Cl.
*A61B 6/00* (2006.01)
*G06F 3/16* (2006.01)

(52) U.S. Cl.
CPC .............. *A61B 6/467* (2013.01); *A61B 6/468* (2013.01); *A61B 6/54* (2013.01); *G06F 3/167* (2013.01); *A61B 6/4405* (2013.01); *A61B 6/563* (2013.01)

(58) Field of Classification Search
CPC . A61B 5/369; A61B 2017/00203; A61B 5/74; A61B 6/548; A61B 6/032; A61B 6/03; A61B 8/13
See application file for complete search history.

(56) References Cited

U.S. PATENT DOCUMENTS

| 9,713,455 | B2 | 7/2017 | Garcia et al. |
| 2004/0086163 | A1 | 5/2004 | Moriyama et al. |

(Continued)

FOREIGN PATENT DOCUMENTS

| CN | 102247154 A | 11/2011 |
| CN | 202077103 U | 12/2011 |

(Continued)

OTHER PUBLICATIONS

The Extended European Search Report in European Application No. 19851317.8 dated Jul. 30, 2021, 7 pages.

(Continued)

*Primary Examiner* — Don K Wong
(74) *Attorney, Agent, or Firm* — METIS IP LLC

(57) ABSTRACT

The present disclosure is related to systems and methods for controlling an imaging device. The system may include an imaging device, a voice processing device, and a terminal. The imaging device may be configured to image a subject. The voice processing device may be configured to receive a first voice signal from or transmit a second voice signal to the subject when the subject is positioned within the imaging device. The terminal may be configured to receive a third voice signal from or transmit a fourth voice signal to a user.

19 Claims, 9 Drawing Sheets

(56) References Cited

U.S. PATENT DOCUMENTS

| | | |
|---|---|---|
| 2005/0197565 A1 | 9/2005 | Yagi et al. |
| 2011/0288853 A1 | 11/2011 | Butzine et al. |
| 2015/0237222 A1 | 8/2015 | Haider et al. |

FOREIGN PATENT DOCUMENTS

| | | | |
|---|---|---|---|
| CN | 103202700 A | 7/2013 | |
| CN | 203841707 U | 9/2014 | |
| CN | 204049665 U | 12/2014 | |
| CN | 104347063 A | 2/2015 | |
| CN | 204863234 U | 12/2015 | |
| CN | 105245857 A | 1/2016 | |
| CN | 106264574 A | 1/2017 | |
| CN | 106308828 A | 1/2017 | |
| CN | 106361364 A | 2/2017 | |
| CN | 109009186 A | 12/2018 | |
| CN | 109124664 A | 1/2019 | |
| CN | 110648683 A | 1/2020 | |
| DE | 102015201354 B4 * | 11/2016 | ............. A61B 5/055 |
| EP | 1416412 A2 | 5/2004 | |
| JP | H0617707 U | 3/1994 | |
| JP | 2004016784 A | 1/2004 | |
| JP | 2004041489 A | 2/2004 | |
| JP | 2005087612 A | 4/2005 | |

OTHER PUBLICATIONS

International Search Report in PCT/CN2019/102349 dated Oct. 22, 2019, 5 pages.
Written Opinion in PCT/CN2019/102349 dated Oct. 22, 2019, 5 pages.

\* cited by examiner

SYSTEMS AND METHODS FOR CONTROLLING IMAGING DEVICE

CROSS-REFERENCE TO RELATED APPLICATIONS

This application is a Continuation of International Application No. PCT/2019/102349, filed on Aug. 23, 2019, which claims priority of Chinese Patent Application No. 201811109281.9 filed on Sep. 21, 2018, and Chinese Patent Application No. 201810966308.X, filed on Aug. 23, 2018, the contents of each of which are hereby incorporated by reference.

TECHNICAL FIELD

This disclosure generally relates to an imaging device, and more particularly, relates to systems and methods for controlling an imaging device via a terminal.

BACKGROUND

Medical imaging systems, such as an X-ray imaging device, have been widely used in clinical examinations and medical diagnoses in recent years. Digital radiography (DR) is an advanced X-ray imaging device that combines computer digital image processing technology with X-ray radiation technology. Digital radiography has multiple advantages, such as a low radiation dose, a high image quality, a high disease detection rate and diagnostic accuracy. Furthermore, a mobile digital radiography can be moved over a wide range to meet scanning needs of different portions of a patient with impaired mobility.

When using an X-ray imaging device to perform a scan, a user (e.g., a doctor, a technician) needs to control the X-ray imaging device. For example, the user may adjust one or more components of the X-ray imaging device to capture image data (e.g., a front view image, a side view image) of a subject (e.g., a patient). As another example, the user may control an imaging parameter (e.g., an exposure time) and process the captured image data via an operation platform installed in the X-ray imaging device, which may both cause unnecessary radiation to the user.

In addition, to perform an imaging, the X-ray imaging device needs to be moved from a storage location to a location of the subject. After completing the imaging, the X-ray imaging device also needs to be moved to a network coverage area to upload the captured image data to a management system (e.g., a picture archiving and communication systems (PACS)). During an imaging process, the X-ray imaging device may need to be moved frequently. Due to a relatively large volume of the X-ray imaging device, it may be time consuming and laborious to move the X-ray imaging device, resulting in a low flexibility and/or availability of the mobile imaging. Furthermore, a communication between the subject and the user is inconvenient, so that timely exchange of information between the subject and the user may be difficult, which in turn may reduce the efficiency and/or effectiveness of the use of the X-ray imaging device.

Therefore, it is desirable to provide systems and methods for controlling the imaging device to facilitate the communication between the subject and the user and improve the flexibility and/or availability of mobile imaging.

SUMMARY

According to an aspect of the present disclosure, a system is provided. The system may include an imaging device, a voice processing device, and a terminal. The imaging device may be configured to image a subject. The voice processing device may be configured to receive a first voice signal from or transmit a second voice signal to the subject when the subject is positioned within the imaging device. The terminal may be configured to receive a third voice signal from or transmit a fourth voice signal to a user.

In some embodiments, the system may include an image capture device. The image capture device may be configured to capture an image representing a status of the subject when the subject is positioned within the imaging device.

In some embodiments, the image capture device may be mounted on the imaging device.

In some embodiments, the system may include a storage device, in communication with the terminal, configured to store information including or relating to at least one of the first voice signal, the second voice signal, the third voice signal, the fourth voice signal, or a recorded voice signal. The terminal may be configured to transmit at least a portion of the information stored in the storage device to at least one of the subject or the user.

In some embodiments, the voice processing device may include at least one of a speaker, a microphone, or an integrated device including the speaker and the microphone.

In some embodiments, the voice processing device may be mounted on the imaging device.

In some embodiments, the terminal may include a second voice processing device.

In some embodiments, the second voice processing device may include at least one of a speaker, a microphone, or an integrated device including the speaker and the microphone.

In some embodiments, the terminal may be configured to receive an instruction provided by the user for controlling the imaging of the subject by the imaging device.

In some embodiments, the terminal may include an exposure control unit. The exposure control unit may be configured to adjust an exposure parameter and transmit a command for adjusting the exposure parameter to the imaging device.

In some embodiments, the terminal may include a movement control unit. The movement control unit may be configured to transmit to the imaging device a second command for controlling a movement of at least one component of the imaging device.

In some embodiments, the terminal may be removably attached to the imaging device.

In some embodiments, the terminal may be a portable tablet.

In some embodiments, the imaging device may be an X-ray imaging device.

In some embodiments, the imaging device may be a mobile digital radiography (DR) or a C-arm device.

In some embodiments, the imaging device may include an X-ray source, a detector. The X-ray source may include a high voltage generator and a tube. The terminal may be in communication with the high voltage generator and the tube to transmit a control signal. The system may further include an exposure synchronization module configured to synchronize the high voltage generator and the detector based on the control signal. The imaging device may be configured to generate image data by imaging the subject based on the control signal and synchronization between the high voltage generator and the detector. The terminal may be configured to obtain, process, and transmit the image data.

In some embodiments, the system may include a first transceiver, a second transceiver, and a third transceiver. The first transceiver may be configured to transmit the control signal and receive second information from at least one of the high voltage generator or the tube. The second transceiver may be configured to transmit third information of the high voltage generator, and receive fourth information from at least one of the terminal or the tube. The third transceiver may be configured to transmit fifth information of the detector, and receive sixth information from at least one of the terminal or the high voltage generator.

In some embodiments, the terminal may further be configured to obtain a status of the high voltage generator.

In some embodiments, the terminal may further be configured to obtain a status of the detector.

In some embodiments, the status of the detector may include at least one of a connection status, a readiness status, power information, temperature information, or error information.

In some embodiments, communication between at least two of the imaging device, the voice processing device, or the terminal may be wireless.

In some embodiments, the wireless communication may include at least one of a Wi-Fi, a Bluetooth, a radio frequency transmission, or an infrared transmission.

In some embodiments, the system may include a picture archiving and communication system (PACS). At least one of the imaging device, or the terminal may further be configured to communicate with the PACS.

According to another aspect of the present disclosure, a system is provided. The system may include an imaging device, a terminal, and an exposure synchronization module. The imaging device may include an X-ray source and a detector. The X-ray source may include a high voltage generator and a tube. The terminal, in communication with the high voltage generator and the tube, may be configured to transmit a control signal. The exposure synchronization module may be configured to synchronize the high voltage generator and the detector based on the control signal. The imaging device may be configured to generate image data by imaging a subject based on the control signal and synchronization between the high voltage generator and the detector. The terminal may be configured to obtain, process, and transmit the image data.

In some embodiments, the system may include a first transceiver, a second transceiver, and a third transceiver. The first transceiver may be configured to transmit the control signal and receive information from at least one of the high voltage generator or the tube. The second transceiver may be configured to transmit second information of the high voltage generator, and receive third information from at least one of the terminal or the tube. The third transceiver may be configured to transmit fourth information of the detector, and receive fifth information from at least one of the terminal or the high voltage generator.

In some embodiments, the terminal may further be configured to obtain a status of the high voltage generator.

In some embodiments, the terminal may further be configured to obtain a status of the detector.

In some embodiments, the status of the detector may include at least one of a connection status, a readiness status, power information, temperature information, or an error information.

In some embodiments, the system may include a voice processing device configured to receive a first voice signal from or transmit a second voice signal to the subject when the subject is positioned within the imaging device. The terminal may be configured to receive a third voice signal from or transmit a fourth voice signal to a user.

In some embodiments, the system may include an image capture device configured to capture an image representing a status of the subject when the subject is positioned within the imaging device.

In some embodiments, the image capture device may be mounted on the imaging device.

In some embodiments, the system may include a storage device, in communication with the terminal, configured to store sixth information including or relating to at least one of the first voice signal, the second voice signal, the third voice signal, the fourth voice signal, or a recorded voice signal. The terminal may be configured to transmit at least a portion of the information stored in the storage device to at least one of the subject or the user.

In some embodiments, the voice processing device may include at least one of a speaker, a microphone, or an integrated device including the speaker and the microphone.

In some embodiments, the voice processing device may be mounted on the imaging device.

In some embodiments, the terminal may include a second voice processing device.

In some embodiments, the second voice processing device includes at least one of a speaker, a microphone, or an integrated device including the speaker and the microphone.

In some embodiments, the terminal may be configured to receive an instruction provided by the user for controlling the imaging of the subject by the imaging device.

In some embodiments, the terminal may include an exposure control unit. The exposure control unit may be configured to adjust an exposure parameter and transmit a command for adjusting the exposure parameter to the imaging device.

In some embodiments, the terminal may include a movement control unit. The movement control unit may be configured to transmit to the imaging device a second command for controlling a movement of at least one component of the imaging device.

In some embodiments, the terminal may be removably attached to the imaging device.

In some embodiments, the terminal may be a portable tablet.

In some embodiments, the imaging device may be an X-ray imaging device.

In some embodiments, the imaging device may be a mobile digital radiography (DR) or a C-arm device.

In some embodiments, communication between at least two of the imaging device, the exposure synchronization module, or the terminal may be wireless.

In some embodiments, the wireless communication may include at least one of a Wi-Fi, a Bluetooth, a radio frequency transmission, or an infrared transmission.

In some embodiments, the system may include a picture archiving and communication system (PACS). At least one of the imaging device, or the terminal may further be configured to communicate with the PACS.

According to another aspect of the present disclosure, a terminal is provided. The terminal may include a storage device, an interface, and a transceiver. The storage device may be configured to store at least one imaging protocol. The interface may be configured to generate a control signal based on a selected imaging protocol from the at least one imaging protocol. The transceiver may be configured to transmit the control signal to an imaging device, and obtain image data associated with a subject. The interface may be configured to display the image data.

In some embodiments, the terminal may include a processor configured to process the image data.

In some embodiments, the storage device may be configured to store information associated with the subject.

According to still another aspect of the present disclosure, a method implemented on a computing device having one or more processors and one or more storage devices. The method may include transmitting, by a terminal, a control signal to an imaging device. The imaging device may include an X-ray source and a detector. The X-ray source may include a high voltage generator and a tube. The method may include performing, by an exposure synchronization module, a synchronization operation on the high voltage generator and the detector based on the control signal. The method may include generating, by the imaging device, image data based on the control signal and synchronization between the high voltage generator and the detector. The method may include obtaining, by the terminal, the image data.

In some embodiments, the method may include processing, by the terminal, the image data.

In some embodiments, the method may include transmitting, by the terminal, the image data.

In some embodiments, communication between at least two of the imaging device, the exposure synchronization module, or the terminal may be wireless.

The present disclosure provides a system including an imaging device, a first voice processing device, a terminal, and a second voice processing device. When the terminal is separated from the imaging device, the terminal may transmit data to the imaging device wirelessly. A two-way communication between a subject (e.g., a patient) and a user (e.g., a doctor, a technician) may be achieved via the first voice processing device and the second voice processing device. When the user takes the terminal away from the subject to perform an exposure detection, the user and the subject may undergo an audio communication to achieve a timely and effective information exchange. Therefore, the user may know the needs of the subject in real time, the real-time communication between the user and the subject may be achieved, which may improve the efficiency and/or effectiveness of the imaging process, and save time.

Furthermore, the use of the first voice processing device, the second voice processing device, and the image capture device may combine information in the form of audio and video. When the user is in communication with the subject, real-time image information, video and audio information of the subject may also be acquired.

In addition, in some embodiments, the imaging device may include an X-ray imaging device that in turn includes a high voltage generator and a tube. In some embodiments, the terminal may be in communication with the high voltage generator and the tube wirelessly to transmit a control signal. The imaging device may generate image data by imaging the subject based on the control signal and synchronization between the high voltage generator and the tube. The terminal may obtain, process, and transmit at least a portion of the image data. In the system disclosed in the present disclosure, the imaging device may be controlled via the terminal and the image data may also be processed via the terminal. Due to the wireless communication between the terminal and the imaging device, the terminal may be used away from the imaging device. The imaging device does not need to be moved to a network coverage area to upload the captured image data to a management system (e.g., a picture archiving and communication systems (PACS)). Therefore, the imaging device does not need to be moved frequently, and the image data may be processed conveniently and quickly, which may improve the flexibility and/or availability of mobile imaging.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
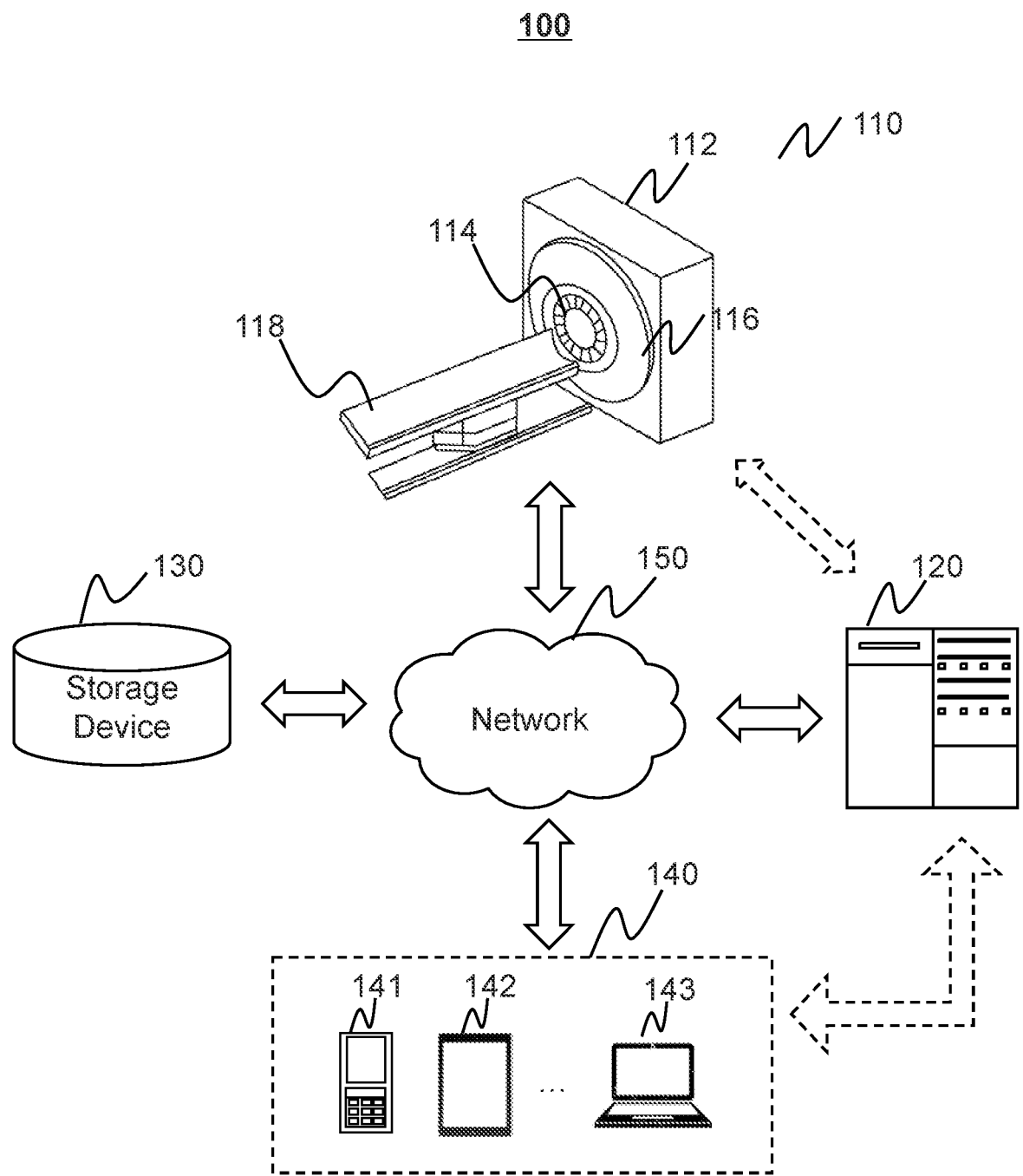
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure, Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device, Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral," "above," "below," "upward(s)," "downward(s)," "left-hand side," "right-hand side," "horizontal," and other such spatial reference terms are used in a relative sense to describe the positions or orientations of certain surfaces/parts/components of the imaging device with respect to other such features of the imaging device when the imaging device is in a normal operating position and may change if the position or orientation of the imaging device changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to a system. The system may include an imaging device, a first voice processing device, and a terminal. The imaging device (e.g., an X-ray imaging device) may be configured to image a subject (e.g., a patient). The first voice processing device may be configured to receive a first voice signal from or transmit a second voice signal to the subject when the subject is positioned within the imaging device. In some embodiments, the terminal may include a second voice processing device. The second voice processing device of the terminal may be configured to receive a third voice signal from or transmit a fourth voice signal to a user. Accordingly, the subject and a user (e.g., a doctor, a technician) may be in communication with each other via the first voice processing device and the terminal (e.g., the second voice processing device), which may improve the efficiency of the imaging device, and may also save time. In some embodiments, the system may further include an image capture device configured to capture an image representing a status of the subject when the subject is positioned within the imaging device. The use of the first voice processing device, the second voice processing device, and the image capture device may combine information in the form of audio and video. When the user is in communication with the subject, the real-time status of the subject may also be acquired. When the user performs an imaging operation (e.g., an exposure detection) on the subject by the imaging device, the user and the subject may undergo an audio communication to achieve a timely and effective information exchange. Therefore, the user may know the needs of the subject in real time, the real-time communication between the user and the subject may be achieved.

For illustration purposes, the imaging device may include an X-ray source and a detector. The X-ray source may include a high voltage generator and a tube. The terminal may be in communication with the high voltage generator and the tube to transmit a control signal. An exposure synchronization module may be configured to synchronize the high voltage generator and the detector based on the control signal. The imaging device may be configured to generate image data by imaging the subject based on the control signal and synchronization between the high voltage generator and the detector. The terminal may be configured to obtain, process, and transmit at least a portion of the image data. Accordingly, the imaging device may be controlled via the terminal and the image data may also be processed via the terminal. Due to a wireless communication between the terminal and the imaging device, the terminal may be used (e.g., process the image data, upload the image data) away from the imaging device. The imaging device does not need to be moved to a network coverage area to upload the captured image data to a management system (e.g., a picture archiving and communication systems (PACS)). Therefore, the imaging device does not need to be moved frequently, and the image data may be processed conveniently and quickly, which may improve the flexibility and/or availability of mobile imaging.

FIG. 1 is a schematic diagram illustrating an exemplary imaging system according to some embodiments of the present disclosure. As shown, the imaging system 100 may include an imaging device 110, a processing device 120, a storage device 130, one or more terminal(s) 140, and a network 150. In some embodiments, the imaging device 110, the processing device 120, the storage device 130, and/or the terminal(s) 140 may be connected to and/or communicate with each other via a wireless connection (e.g., the network 150), a wired connection, or a combination thereof. The connection between the components in the imaging system 100 may be variable. For example, the imaging device 110 may be connected to the processing device 120 through the network 150, or connected to the processing device 120 directly. As another example, the storage device 130 may be connected to the processing device 120 through the network 150, as illustrated in FIG. 1, or connected to the processing device 120 directly. As still another example, the terminal(s) 140 may be connected to the processing device 120 through the network 150, or connected to the processing device 120 directly. As still another example, the terminal(s) 140 may be connected to the imaging device 110 through the network 150, as illustrated in FIG. 1, or connected to the imaging device 110 directly.

The imaging device 110 may be configured to scan a subject using radiation rays and generate imaging data used to generate one or more images relating to the subject. In some embodiments, the imaging device 110 may transmit the imaging data to the processing device 120 or the terminal 140 for further processing (e.g., generating one or more images). In some embodiments, the imaging data and/or the one or more images associated with the subject may be stored in the storage device 130, the processing device 120, and/or the terminal 140.

In some embodiments, the imaging device 110 may be a computed tomography (CT) scanner, a suspended X-ray imaging device, a digital radiography (DR) scanner (e.g., a mobile digital X-ray imaging device), a C-arm device, a digital subtraction angiography (DSA) scanner, a dynamic spatial reconstruction (DSR) scanner, an X-ray microscopy scanner, a multimodality scanner, or the Ike, or any combination thereof. Exemplary multi-modality scanners may include a computed tomography-positron emission tomography (CT-PET) scanner, a computed tomography-magnetic resonance imaging (CT-MRI) scanner, etc. The subject may be biological or non-biological. In some embodiments, the subject may include a patient, a man-made object, etc. In some embodiments, the subject may include a specific portion, organ, and/or tissue of a patient. For example, the subject may include head, brain, neck, body, shoulder, arm, thorax, cardiac, stomach, blood vessel, soft tissue, knee, feet, or the Ike, or any combination thereof.

In some embodiments, the imaging device 110 may include a gantry 112, a detector 114, a radiation source 116, and a table 118. The subject may be placed on the table 118 for scanning. In some embodiments, the radiation source 116 may include a high voltage generator (not shown in FIG. 1), a tube (not shown in FIG. 1) and a collimator (not shown in FIG. 1). The high voltage generator may be configured to generate a high-voltage and current for the tube. The tube may generate and/or emit radiation beams traveling toward the subject. The radiation may include a particle ray, a photon ray, or the like, or any combination thereof. In some embodiments; the radiation may include a plurality of radiation particles (e.g., neutrons, protons, electron, p-mesons, heavy ions), a plurality of radiation photons (e.g., X-ray, a y-ray, ultraviolet, laser), or the like, or any combination thereof. In some embodiments, the tube may include an anode target and a filament. The filament may be configured to generate electrons to bombard the anode target. The anode target may be configured to generate the radiation rays (e.g.; X-rays) when the electrons bombard the anode target. The collimator may be configured to adjust the irradiation region (i.e., radiation field) on the subject. The collimator may also be configured to adjust the intensity and/or the number (or count) of the radiation beams that irradiate on the subject.

The detector 114 may detect radiation beams. In some embodiments, the detector 114 may be configured to produce an analog electrical signal that represents the intensity of the received X-rays, including the attenuated beam, as it passes through the subject. In some embodiments, the detector 114 may be a flat panel detector. In some embodiments, the detector 114 may include a plurality of detecting units. The detecting units may include a scintillation detector (e.g., a cesium iodide detector), a gas detector; etc. The plurality of detecting units of the detector may be arranged in any suitable manner, for example, a single row, two rows, or another number of rows. More descriptions of components in the imaging device 110 may be found elsewhere in the present disclosure (e.g., FIG. 2 and the descriptions thereof).

The processing device 120 may process data and/or information obtained from the imaging device 110, the storage device 130, and/or the terminal(s) 140. For example, the processing device 120 may reconstruct an image relating to at least one part of a subject (e.g., a tumor) based on imaging data collected by the imaging device 110. As another example, the processing device 120 may process image data collected by the imaging device 110. In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140.

The storage device 130 may store data, instructions, and/or any other information. In some embodiments, the storage device 130 may store data obtained from the imaging device 110, the processing device 120, and/or the terminal(s) 140. For example, the storage device 130 may store information associated with a subject. The information associated with the subject may include a name of the subject, the gender of the subject, the age of the subject, a portion of the subject to be imaged, or the like, or any combination thereof. As another example, storage device 130 may store an imaging parameter associated with at least one component of the imaging system 100, The imaging parameter may include a current of an imaging device, a voltage of an imaging device, a scan time, or the like, or any combination thereof. As still another example, the storage device 130 may store at least one imaging protocol. The imaging protocol may refer to a combination of various imaging parameters. In some embodiments, the imaging protocol may be determined based on hardware and software of the imaging device, a user's preference, the information associated with the subject. As still another example, the storage device 130 may store a status of at least one component of the imaging system 100. The status of the at least one component (e.g., a high voltage generator, the detector 114) of the imaging system 100 may include a connection status, a readiness status, power information, temperature information, error information, or the like, or any combination thereof. As still another example, the storage device 130 may store information including or relating to at least one of a first voice signal, a second voice signal, a third voice signal, a fourth voice signal, or a recorded voice signal, as described elsewhere in the present disclosure. The recorded voice signal may be pre-recorded by the user. The information relating to the first voice signal (or the second voice signal, the third voice signal, the fourth voice signal, the recorded voice signal) may include a processed first voice signal (or a processed second voice signal, a processed third voice signal, a processed fourth voice signal, a processed recorded voice signal). In some embodiments, the storage device 130 may store data and/or instructions that the processing device 120 and/or the terminal 140 may execute or use to perform exemplary methods described in the present disclosure. In some embodiments, the storage device 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the imaging system 100 (e.g., the processing device 120, the terminal(s) 140). One or more components in the imaging system 100 may access the data or instructions stored in the storage device 130 via the network 150. In some embodiments, the storage device 130 may be part of the processing device 120. In some embodiments, the storage device 130 may be part of the terminal 140.

Figure 2:
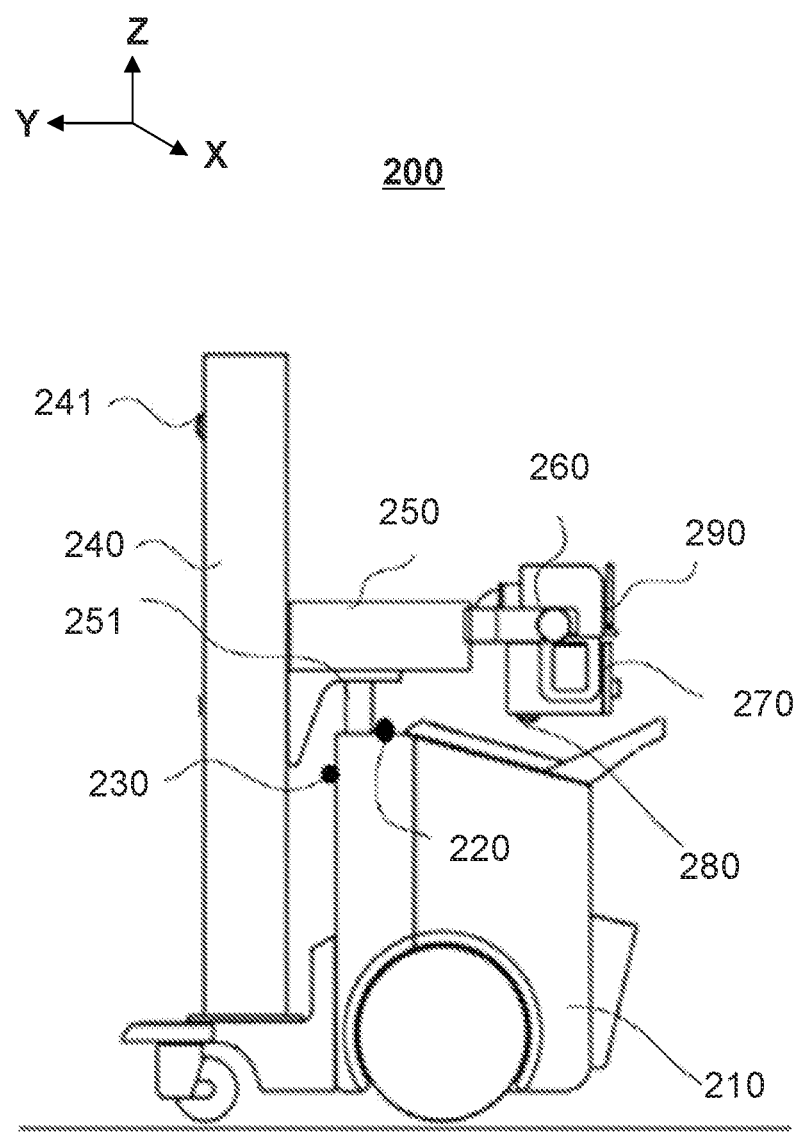
FIG. 2 is a schematic diagram illustrating an exemplary imaging device according to some embodiments of the present disclosure.

In some embodiments, the imaging system 100 may further include a first voice processing device (e.g., a speaker 220, a microphone 230 as illustrated in FIG. 2). The first voice processing device may be configured to receive a first voice signal from or transmit a second voice signal to the subject when the subject is positioned within the imaging device 110. For example, the first voice processing device may transmit the first voice signal received from the subject to the terminal 140. As another example, the first voice processing device may transmit the second voice signal received from the terminal 140 to the subject.

In some embodiments, the first voice processing device may include a speaker, a microphone, an integrated device including the speaker and the microphone, or the like, or any combination thereof. The speaker may convert an electrical signal into a voice. The microphone may be a transducer that converts a voice into an electrical signal.

In some embodiments, the first voice processing device may be mounted on the imaging device 110. The first voice processing device may be mounted on a location of the imaging device 110 dose to the subject to ensure an accurate acquisition of voice information (e.g., the first voice signal) from the subject, thereby facilitating the communication between the subject and the user. For example, the first voice processing device may be mounted on a trolley (e.g., a trolley 210 as illustrated in FIG. 2) of the imaging device 110. As another example, the first voice processing device may be mounted on the table 118.

The terminal(s) 140 may be connected to and/or communicate with the imaging device 110, the processing device 120, and/or the storage device 130. For example, the terminal 140 may receive a third voice signal from or transmit a fourth voice signal to a user. As another example, the terminal 140 may obtain, process, and transmit image data collected by the imaging device 110. As still another example, a user may provide an input via a user interface implemented on the terminal 140. The input may include an imaging parameter (e.g., an exposure parameter), an image construction parameter, information associated with the subject to be imaged, as described elsewhere in the present disclosure. As still another example, the terminal 140 may receive an instruction provided by the user for controlling the imaging of the subject by the imaging device 110. As still another example, the terminal 140 may adjust an imaging parameter (e.g., an exposure parameter) and transmit a first command for adjusting the imaging parameter (e.g., the exposure parameter) to the imaging device 110. As still another example, the terminal 140 may transmit to the imaging device 110 a second command for controlling a movement of at least one component of the imaging device 110. As still another example, the terminal 140 may transmit a control signal to the imaging device 110 to control a status of at least one component (e.g., a high voltage generator, a tube, a detector) of the imaging device 110. The status of the at least one component of the imaging device 110 may include a connection status, a readiness status, power information, temperature information, error information, or the like, or any combination thereof.

In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof. In some embodiments, software, programs, and/or applications for control signal transmission, image acquisition, image processing, image archiving, image printing, or the like, may be developed based on an operating system of the terminal 140. The software, programs, and/or applications may be activated, operated, and/or perform corresponding work based on a specific signal transmitted from the imaging device 110.

Figure 3:
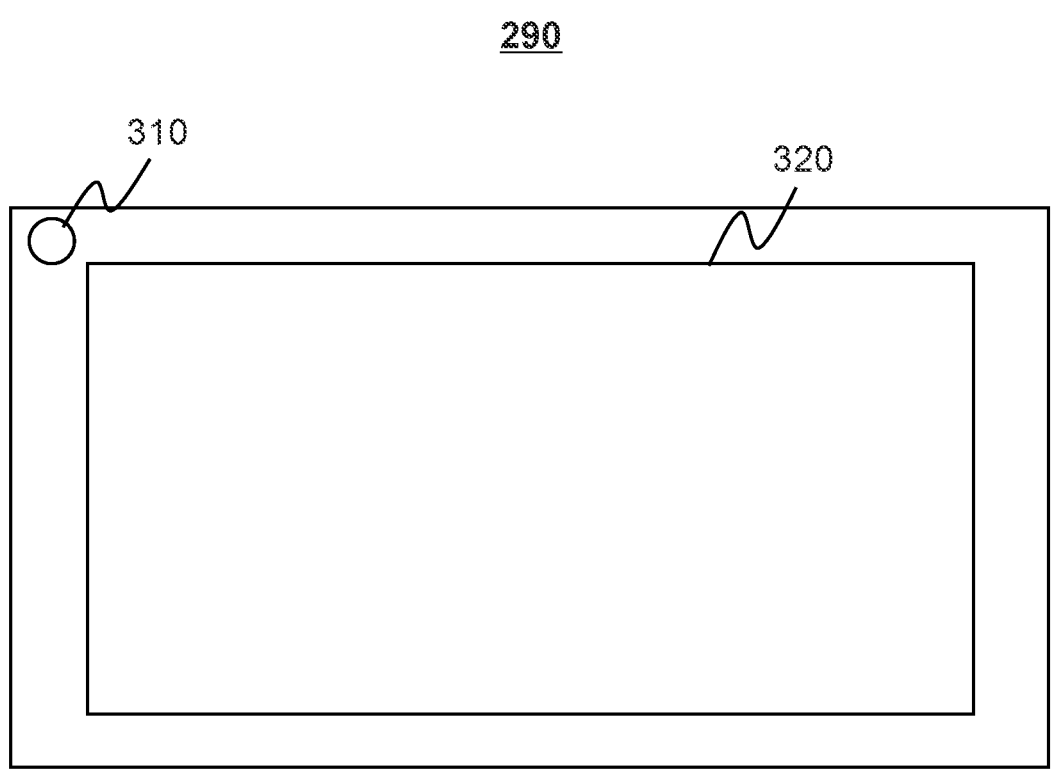
FIG. 3 is a schematic diagram illustrating an exemplary terminal according to some embodiments of the present disclosure.

In some embodiments, the terminal 140 may include a second voice processing device (e.g., a voice processing device 310 as illustrated in FIG. 3). The second voice processing device may include a speaker, a microphone, an integrated device including the speaker and the microphone, or the like, or any combination thereof. The second voice processing device may receive a third voice signal from or transmit a fourth voice signal to a user. For example, the second voice processing device may transmit the third voice signal received from the user to the first voice processing device. As another example, the second voice processing device may transmit the fourth voice signal received from the first voice processing device to the user. Accordingly, a two-way communication or a one-way communication between the subject and the user may be achieved via the first voice processing device and the second voice processing device. More descriptions of the second voice processing device may be found elsewhere in the present disclosure (e.g., FIG. 3 and descriptions thereof).

In some embodiments, the terminal 140 may be removably attached to the imaging device 110. In this situation, the terminal 140 may communicate with the imaging device 110, the processing device 120, and/or the storage device 130 wirelessly. When the user takes the terminal 140 away from the subject to perform an exposure detection, the user and the subject may undergo an audio communication to achieve a timely and effective information exchange. Therefore, the user may know the needs of the subject in real time, the real-time communication between the user and the subject may be achieved, which may improve the efficiency and/or effectiveness of the imaging process, and may also save time.

Accordingly, the terminal 140 disclosed in the present disclosure may replace a console in a traditional imaging device. The terminal 140 may be in communication with one or more other components of the imaging system 100 via a wireless connection. After the imaging of the subject is completed, the user may take the terminal 140 and be away from the imaging device 110, the image data collected by the imaging device 110 may be obtained, processed, and transmitted by the user via the terminal 140.

The network 150 may include any suitable network that can facilitate the exchange of information and/or data for the imaging system 100. In some embodiments, one or more components of the imaging system 100 (e.g., the imaging device 110, the processing device 120, the storage device 130, the terminals) 140, etc.) may communicate information and/or data with one or more other components of the imaging system 100 via the network 150. For example, the processing device 120 and/or the terminal 140 may obtain image data from the imaging device 110 via the network 150. As another example, the processing device 120 and/or the terminal 140 may obtain information stored in the storage device 130 via the network 150. As still another example, the processing device 120 and/or the terminal 140 may transmit a control signal to the imaging device 110 via the network 150. As still another example, the processing device 120 and/or the terminal 140 may obtain a status of at least one component (e.g., a high voltage generator, a tube, a detector) of the imaging device 110 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the storage device 130 may be a data storage including cloud computing platforms, such as public cloud, private cloud, community, and hybrid clouds, etc. As another example, the processing device 120 may be integrated into the terminal(s) 140. As still another example, the imaging system 100 may further include an image capture device (e.g., an image capture device 280 as illustrated in FIG. 2) configured to capture an image representing a status of the subject when the subject is positioned within the imaging device 110.

In some embodiments, the imaging system 100 may include a picture archiving and communication system (PACS). The PACS may be a medical imaging technology which provides economical storage and convenient access to images from multiple modalities (source machine types). Images and reports in the form of an electronic file may be transmitted digitally via PACS, which may eliminate the need to manually file, retrieve, or transport film jackets, the folders used to store and protect an image in the form of, e.g., an X-ray film. In some embodiments, one or more components of the imaging system 100 may be in communication with the PACS. For example, the terminal 140 may transmit the image data collected by the imaging device 110 to the PACS. Specifically, the terminal 140 may transmit the image data to the PACS by connecting to a medical system or a cloud platform via a wireless connection or a wired connection.

FIG. 2 is a schematic diagram illustrating an exemplary imaging device according to some embodiments of the present disclosure. In some embodiments, the imaging device 200 may be an example of the imaging device 110 or a portion of the imaging device 110. As shown in FIG. 2, the imaging device 200 may include a trolley 210, a speaker 220, a microphone 230, a column 240, an arm 250, a tube shell 260, a collimator 270, an image capture device 280, and a terminal 290. In some embodiments, the terminal 290 may be an example of the terminal 140 or a portion of the terminal 140.

The trolley 210 may be configured to accommodate one or more components of the imaging device 200. For example, the trolley 210 may accommodate a circuit board, a signal processing circuit, and an electronic component of the imaging device 200. In some embodiments, the trolley 210 may include one or more rolling devices (e.g., one or more wheels). The trolley 210 may move around via the one or more wheels.

The column 240 may be a main supporting component in the imaging device 200. The column 240 may be connected to the trolley 210 via the arm 250. In some embodiments, an end of the arm 250 may be connected to the column 240, and another end of the arm 250 may be connected to the tube shell 260. In some embodiments, the arm 250 may be mounted on the trolley 210 via a locking device 251. The locking device 251 may include a mechanical locking device (e.g., a buckle with a concave and convex structure), an electromagnetic locking device, or the like, or any combination thereof.

In some embodiments, the arm 250 and the tube shell 260 may move with the column 240. For example, the arm 250 and the tube shell 260 may move along an axis that passes through the center of the column 240 and is parallel to a Z axis as illustrated in FIG. 2. The arm 250 and the tube shell 260 may also rotate with the column 240 along an axis that passes through the center of the column 240 and is parallel to the Z-axis. In some embodiments, the arm 250 may be retractable.

The tube shell 260 may be configured to protect one or more components (e.g., a tube) of the imaging device 200. The tube (not shown in FIG. 2) may be configured to emit one or more X-ray beams toward a subject to be imaged. The collimator 270 may be configured to control the irradiation region on the subject. The collimator 270 may also be configured to adjust the intensity and/or the number (or count) of the X-ray beams that irradiate on the subject. The collimator 270 may further be configured to filter one or more scattered rays of the X-ray beams In some embodiments, the collimator 270 may be mounted on the bottom of the tube shell 260, as illustrated in FIG. 2.

The image capture device 280 may be configured to acquire image data (e.g., a video, an image) of the subject to be imaged. In some embodiments, the image capture device 280 may capture an image representing a real time status of the subject when the subject is positioned within the imaging device 200. The status of the subject may include a position of the subject, a posture of the subject, or the like. In some embodiments, the image capture device 280 may acquire the image data of a certain range in a same direction as the X-rays beams emitted by the collimator 270.

In some embodiments, the image capture device 280 may be mounted on the imaging device 200. For example, the image capture device 280 may be mounted on the collimator 270. As another example; the image capture device 280 may be connected to the arm 250 via a movable robotic arm. The field of view of the image capture device 280 may be adjusted by adjusting the direction and the angle of the movable robotic arm. In some embodiments, the image capture device 280 may be and/or include any suitable device that is capable of acquiring image data, Exemplary image capture devices 280 may include a camera (e.g., a digital camera, an analog camera, etc.), a video recorder, a mobile phone, a tablet computing device, a wearable computing device, an infrared imaging device (e.g., a thermal imaging device), or the like.

The camera 241 mounted on the column 240 may be configured to capture image data (e.g., a video, an image) of the scene in front of the column 240. The image data captured by the camera 241 may be transmitted to one or more components (e.g., the terminal 290) for display. The user may get to know the road condition in front of the column 240 via the terminal 290 when he or she pushes the imaging device 200.

A first voice processing device may include the speaker 220, the microphone 230, or an integrated device including the speaker and the microphone. The first voice processing device may be mounted on the imaging device 200. For example, the speaker 220 and the microphone 230 may be mounted on the trolley 210. The first voice processing device may be configured to receive a first voice signal from or transmit a second voice signal to the subject when the subject is positioned within the imaging device 200. For example, the first voice processing device (e.g., the microphone 230) may transmit the first voice signal received from the subject to the terminal 290. As another example, the first voice processing device (e.g., the speaker 220) may transmit the second voice signal received from the terminal 290 to the subject.

The terminal 290 may be configured to control the imaging device 200. The terminal 290 may be the same as or similar to the terminal 140 as described in connection with FIG. 1, In some embodiments, the terminal 290 may be a portable tablet mounted on the imaging device 200. In some embodiments; the terminal 290 may be removably attached to the imaging device 200. For example; when the terminal 290 is not in use, the terminal 290 may be stored in a container (not shown in FIG. 2) mounted on the tube shell 260. During the imaging of the subject, the user may take the terminal 290 from the container, carry and use it, e.g., to control one or more components of the imaging device 200, while the user is away from imaging device 200 and the subject. More descriptions of the terminal 290 may be found elsewhere in the present disclosure (e.g., FIG. 3, and descriptions thereof).

In some embodiments, the imaging device 200 may include the image capture device 280 and the first voice processing device so that the imaging device 200 may both acquire image data of the subject and receive the first voice signal from or transmit the second voice signal to the subject when the subject is positioned within the imaging device 200 and facilitate a real-time two-way communication between the subject and the user. In some embodiments, the speaker 220 and the microphone 230 may be integrated into a single component, which may both receive the first voice signal from or transmit the second voice signal to the subject when the subject is positioned within the imaging device 200.

In some embodiments, the first voice processing device (e.g.; the speaker 220, the microphone 230), the image capture device 280, the terminal 290, and/or one or more other components of the imaging device 200 may be connected to and/or communicate with each other via a wireless connection (e.g., a Wi-Fi, a Bluetooth, a radio frequency transmission, an infrared transmission), a wired connection, or a combination thereof. For example, the terminal 290 may be connected to the image capture device 280 or the camera 241 via the network 150. The image data captured by the image capture device 280 or the camera 241 may be transmitted to the terminal 290 for display. As another example, the terminal 290 may be connected to the one or more components (e.g., a tube, a high voltage generator, a detector) of the imaging device 200 via the network 150. The user may control the one or more components of the imaging device 200 via the terminal 290. The image data generated by the imaging device 200 may be transmitted to the terminal 290 for display.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the column 240 may be configured in any suitable manner, such as a C-shape support, a U-shape support, a G-shape support, or the like. In some embodiments, the imaging device 200 may include one or more additional components not described, and/or without one or more components illustrated in FIG. 2. For example, the camera 241 may be omitted. As another example, the imaging device 200 may further include a gantry configured to support one or more components of the imaging device 200, such as, the detector, the collimator 270, and the tube.

In some embodiments, the imaging device 200 may further include a charging device. The charging device may be configured to charge one or more components (e.g., the terminal 290) of the imaging device 200. For example, the charging device may charge the terminal 290 when the terminal 290 is placed in the container mounted on the tube shell 260. As another example, the charging device may charge the terminal 290 via a wired connection (e.g., via a USB port) or a wireless connection.

FIG. 3 is a schematic diagram illustrating an exemplary terminal according to some embodiments of the present disclosure. As shown in FIG. 3, the terminal 290 may include a second voice processing device 310 and a display 320.

The second voice processing device 310 may include a speaker; a microphone, an integrated device including the speaker and the microphone, or the like, or any combination thereof. The second voice processing device 310 may receive a third voice signal from or transmit a fourth voice signal to a user. For example, the second voice processing device 310 (e.g., the microphone) may transmit the third voice signal received from the user to a first voice processing device mounted on an imaging device (e.g., the imaging device 110, the imaging device 200). As another example, the second voice processing device 310 (e.g., the speaker) may transmit the fourth voice signal received from the first voice processing device to the user. A two-way communication or a one-way communication between a subject and the user may be achieved via the first voice processing device mounted on the imaging device and the second voice processing device 310 mounted on the terminal 290.

In some embodiments, a microphone (e.g., the microphone 230) of the first voice processing device mounted on the imaging device (e.g., the imaging device 200) and the speaker of the second voice processing device 310 mounted on the terminal 290 may be configured as a first voice transmission path. For example; the speaker of the second voice processing device 310 mounted on the terminal 290 may convert a first voice of the user into a first electrical signal and transmit the first electrical signal to the first voice processing device mounted on the imaging device (e.g., the imaging device 200). The microphone (e.g., the microphone 230) of the first voice processing device mounted on the imaging device (e.g., the imaging device 200) may convert the first electrical signal into the first voice and transmit the first voice to the subject.

In some embodiments, a speaker (e.g., the speaker 220) of the first voice processing device mounted on the imaging device (e.g., the imaging device 200) and the microphone of the second voice processing device 310 mounted on the terminal 290 may be configured as a second voice transmission path. For example, the speaker (e.g., the speaker 220) of the first voice processing device mounted on the imaging device (e.g., the imaging device 200) may convert a second voice of the subject into a second electrical signal and transmit the second electrical signal to the second voice processing device 310 mounted on the terminal 290. The microphone of the second voice processing device 310 mounted on the terminal 290 may convert the second electrical signal into the second voice and transmit the second voice to the user.

In some embodiments, the first voice processing device may include the microphone (e.g., the microphone 230), and the second voice processing device 310 may include the speaker. In some embodiments, the first voice processing device may include the speaker (e.g., the speaker 220), and the second voice processing device may include the microphone.

In some embodiments, the user may send a real time voice signal to the subject via the first voice processing device and the second voice processing device 310. For example, the user may say "please put your hands down," "that is fine," or the like, to the subject via the first voice processing device and the second voice processing device 310. In some embodiments, the user may send a recorded voice signal to the subject via the first voice processing device and the second voice processing device 310. The recorder voice signal may be pre-recorded by this or another user of the imaging system 100. In some embodiments, the recorded voice signal may include "are you ready," "hello," "please do not move," "please put your hands down," "inhale," "exhale," or the like. In some embodiments, a plurality of recorded voice signals in one or different languages may be stored in a storage device (e.g., the storage device 130) of the imaging system 100. The user may select a recorded voice signal and transmit the selected recorded voice signal to the subject via the first voice processing device and the second voice processing device 310.

The display 320 may be configured to display data associated with the imaging system 100. In some embodiments, the display 320 may display text (e.g., a number, words), an image, a symbol, a mark, a video, or the like, or any combination thereof. For example, the display 320 may display image data captured by, such as a camera (e.g., the camera 241) and an image capture device (e.g., the image capture device 280). As another example, the display 320 may display image data collected by the imaging device (e.g., the imaging device 110, the imaging device 200). As still another example, the display may display an imaging parameter (e.g., an exposure parameter) and a parameter associated with at least one component (e.g., an inclination angle of a tube) of the imaging system 100.

Accordingly, the user may monitor a real-time status of the subject via an image capture device (e.g., the image capture device 280) and the terminal 290, and help the subject adjust his/her status by talking to the subject via the first voice processing device and the second voice processing device 310. The adjusted status of the subject may also be detected by the user via the image capture device and the terminal 290 in real time. The use of the first voice processing device, the second voice processing device 310, and the image capture device may combine information in the form of audio and video. When the user is in communication with the subject, the real-time status of the subject may also be acquired. When the user performs an imaging operation (e.g., an exposure detection) on the subject by the imaging device, the user and the subject may undergo an audio communication to achieve a timely and effective information exchange. Therefore, the user may know the needs of the subject in real time, the real-time communication between the user and the subject may be achieved, which may improve the efficiency and/or effectiveness of the imaging process, and may also save time.

In some embodiments, the terminal 290 may detect the real-time status of the subject automatically. For example, the terminal 290 may detect whether a portion of the subject to be imaged is shaking during the imaging of the subject based on the image data captured by the image capture device. In response to a determination that the portion of the subject is shaking, the terminal 290 may send a notification regarding the status of the subject to the user and/or the subject.

In some embodiments, the imaging device is an X-ray imaging device. The terminal 290 may include an exposure control unit (not shown in FIG. 3). The exposure control unit may be configured to adjust an exposure parameter and transmit a first command for adjusting the exposure parameter to the imaging device (e.g., the imaging device 110, the imaging device 200). The exposure parameter may include an exposure voltage, an exposure time, or the like, or any combination thereof. In some embodiments, the exposure control unit may include a plurality of exposure function keys associated with the exposure parameter. The selection of the exposure function key by the user may cause the terminal 290 to adjust the exposure parameter. For example, the selection of a start exposure key or a stop exposure key may cause the terminal 290 to direct the imaging device to start a scan or stop the scan of the subject. In some embodiments, after the exposure parameter is adjusted, an exposure control signal may be transmitted to the imaging device. The tube of the imaging device may emit one or more X-ray beams toward the subject to be imaged. The detector may produce an analog electrical signal that represents the intensity of the received X-rays, including the attenuated beam, as it passes through the subject. Image data (e.g., a film, an electronic image) associated with the subject may be generated based on the electrical signal. Accordingly, the radiation received by the user may be reduced, the imaging efficiency and the user experience may be improved.

In some embodiments, the terminal 290 may include a movement control unit. The movement control unit may be configured to transmit to the imaging device a second command for controlling a movement of at least one component of the imaging device. In some embodiments, the movement control unit may include a plurality of movement function keys associated with a movement state of the at least one component of the imaging device. The selection of the movement function key by the user may cause the terminal 290 to control the movement state of the at least one component of the imaging device. For example, the selection of a moving forward key or a moving backward key may cause the terminal 290 to direct the imaging device, or a portion thereof, to move forward or move backward.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the second voice processing device 310 may include a storage device. The storage device of the second voice processing device 310 may include a voice module configured to implement a voice communication function of the second voice processing device 130.

In some embodiments, an information exchange between the terminal 290 and the imaging device may be realized according to a voice over Internet protocol (VoIP). As used herein, the VoIP (also called IP telephony) may refer to a methodology and group of technologies for the delivery of voice communications and multimedia sessions over Internet Protocol (IP) networks, such as the Internet.

In some embodiments, a voice processing may be performed by a universal digital signal processor and a field programmable gate array. The use of the digital signal processor may have multiple advantages, such as a simple implementation, portability, and a fast processing speed.

When the voice communication is implemented, a hardware part of the second voice processing device 310 may include an audio chip. An external hardware interface may include an analog port and a digital port. The analog port may be configured to input and output an audio signal, and support a line input and a voice acquisition. In some embodiments, the digital port may include a chip select (CS), a serial digital interface pin (SDIN), a serial clock (SCLK), and a mode pin. The communication between an audio control port and a digital signal processing (DSP) chip may be realized by a multi-channel buffer serial port (McBSP1). The process of converting an analog signal into a digital signal may be referred to as an analog-to-digital conversion, and it may include sampling, quantization, encoding, and pulse code modulation.

Figure 4:
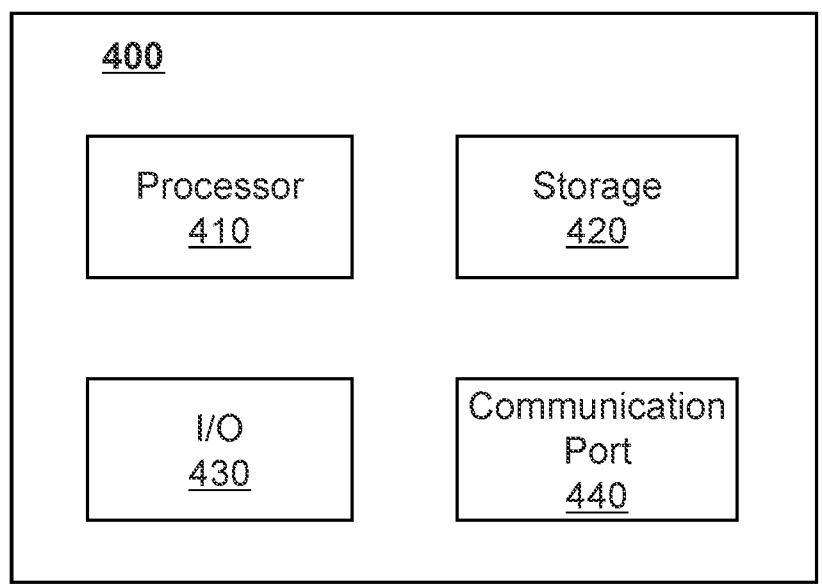
FIG. 4 is a schematic diagram illustrating exemplary hardware and/or software components of an exemplary computing device on which the processing device may be implemented according to some embodiments of the present disclosure.

FIG. 4 is a schematic diagram illustrating exemplary hardware and/or software components of an exemplary computing device 400 on which the processing device 120 may be implemented according to some embodiments of the present disclosure. As illustrated in FIG. 4, the computing device 400 may include a processor 410, a storage 420, an input/output (I/O) 430, and a communication port 440.

The processor 410 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 410 may process imaging data obtained from the imaging device 110, the terminals) 140, the storage device 130, and/or any other component of the imaging system 100. In some embodiments, the processor 410 may include one or more hardware processors, such as a microcontroller, a microprocessor, a reduced instruction set computer (RISC), an application specific integrated circuits (ASICs), an application-specific instruction-set processor (ASID), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 400. However, it should be noted that the computing device 400 in the present disclosure may also include multiple processors. Thus operations and/or method steps that are performed by one processor as described in the present disclosure may also be jointly or separately performed by the multiple processors. For example, if in the present disclosure the processor of the computing device 400 executes both process A and process B, it should be understood that process A and process B may also be performed by two or more different processors jointly or separately in the computing device 400 (e.g., a first processor executes process A and a second processor executes process B, or the first and second processors jointly execute processes A and B).

The storage 420 may store data/information obtained from the imaging device 110, the terminal(s) 140, the storage device 130, and/or any other component of the imaging system 100. The storage 420 may be similar to the storage device 130 described in connection with FIG. 1, and the detailed descriptions are not repeated here.

The I/O 430 may input and/or output signals, data, information, etc. In some embodiments, the I/O 430 may enable a user interaction with the processing device 120. In some embodiments, the I/O 430 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 440 may be connected to a network (e.g., the network 150) to facilitate data communications. The communication port 440 may establish connections between the processing device 120 and the imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a WiFi™ link, a WiMax™ link, a MILAN link, a ZigBee link, a mobile network link (e.g., 3G, 4G, 5G), or the like, or any combination thereof. In some embodiments, the communication port 440 may be and/or include a standardized communication port, such as RS232, RS485. In some embodiments, the communication port 440 may be a specially designed communication port. For example, the communication port 440 may be designed in accordance with the digital imaging and communications in medicine (MOM) protocol.

Figure 5:
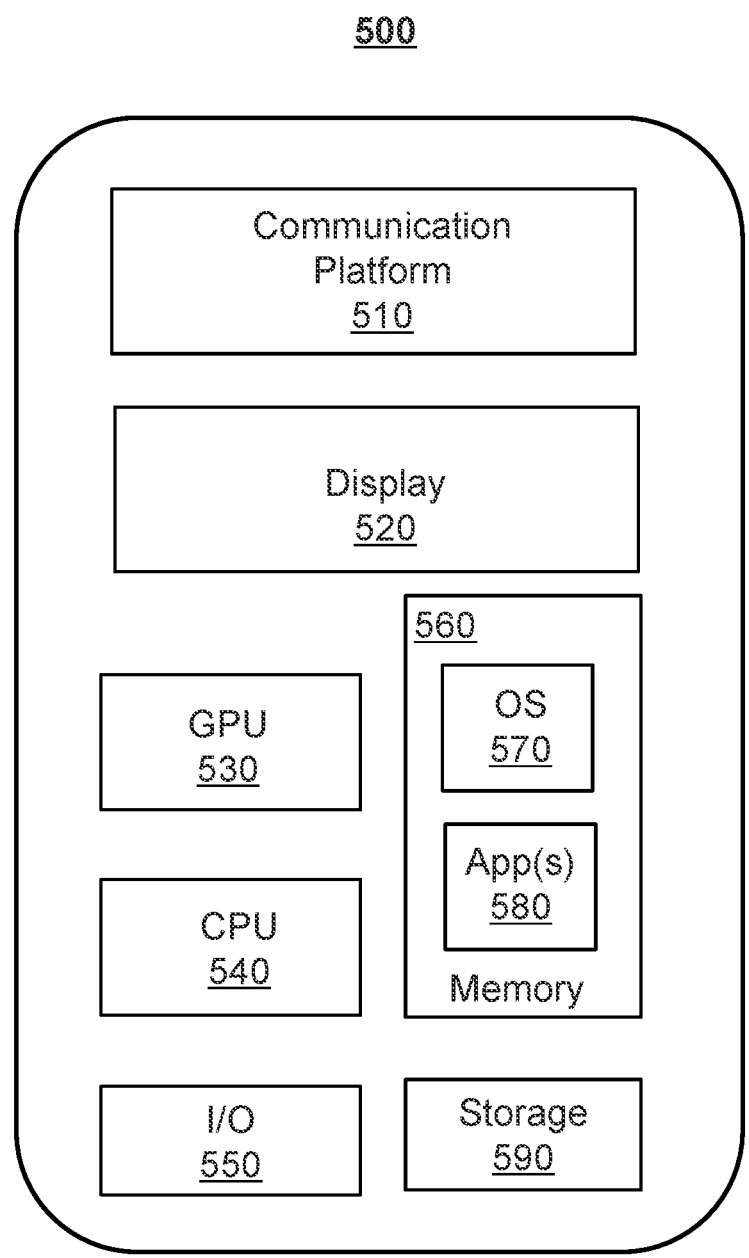
FIG. 5 is a schematic diagram illustrating exemplary hardware and/or software components of an exemplary mobile device on which the terminal(s) may be implemented according to some embodiments of the present disclosure.

FIG. 5 is a schematic diagram illustrating exemplary hardware and/or software components of an exemplary mobile device 500 on which the terminal(s) 140 may be implemented according to some embodiments of the present disclosure.

As illustrated in FIG. 5, the mobile device 500 may include a communication platform 510, a display 520, a graphics processing unit (GPU) 530, a central processing unit (CPU) 540, an I/O 550, a memory 560, and a storage 590. In some embodiments, any other suitable component, including but not limited to a system bus or a controller (not shown), may also be included in the mobile device 500.

In some embodiments, the communication platform 510 may be configured to establish a connection between the mobile device 500 and other components of the imaging system 100, and enable data and/or signal to be transmitted between the mobile device 500 and other components of the imaging system 100. For example, the communication platform 510 may establish a wireless connection between the mobile device 500 and the imaging device 110, and/or the processing device 120. The wireless connection may include, for example, a Bluetooth™ link, a WiFi™ link, a WiMax™ link, a WLAN link, a ZigBee link, a mobile network link (e.g., 3G, 4G, 5G), or the like, or any combination thereof. The communication platform 510 may also enable the data and/or signal between the mobile device 500 and other components of the imaging system 100. For example, the communication platform 510 may transmit data and/or signals inputted by a user to other components of the imaging system 100. The inputted data and/or signals may include a user instruction. As another example, the communication platform 510 may receive data and/or signals transmitted from the processing device 120. The received data and/or signals may include imaging data acquired by a detector of the imaging device 110.

In some embodiments, a mobile operating system (OS) 570 (e.g., iOS™, Android™, Windows Phone™, etc.) and one or more applications (App(s)) 580 may be loaded into the memory 560 from the storage 590 in order to be executed by the CPU 540. The applications 580 may include a browser or any other suitable mobile apps for receiving and rendering information respect to an imaging process or other information from the processing device 120. User interactions with the information stream may be achieved via the I/O 550 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 6:
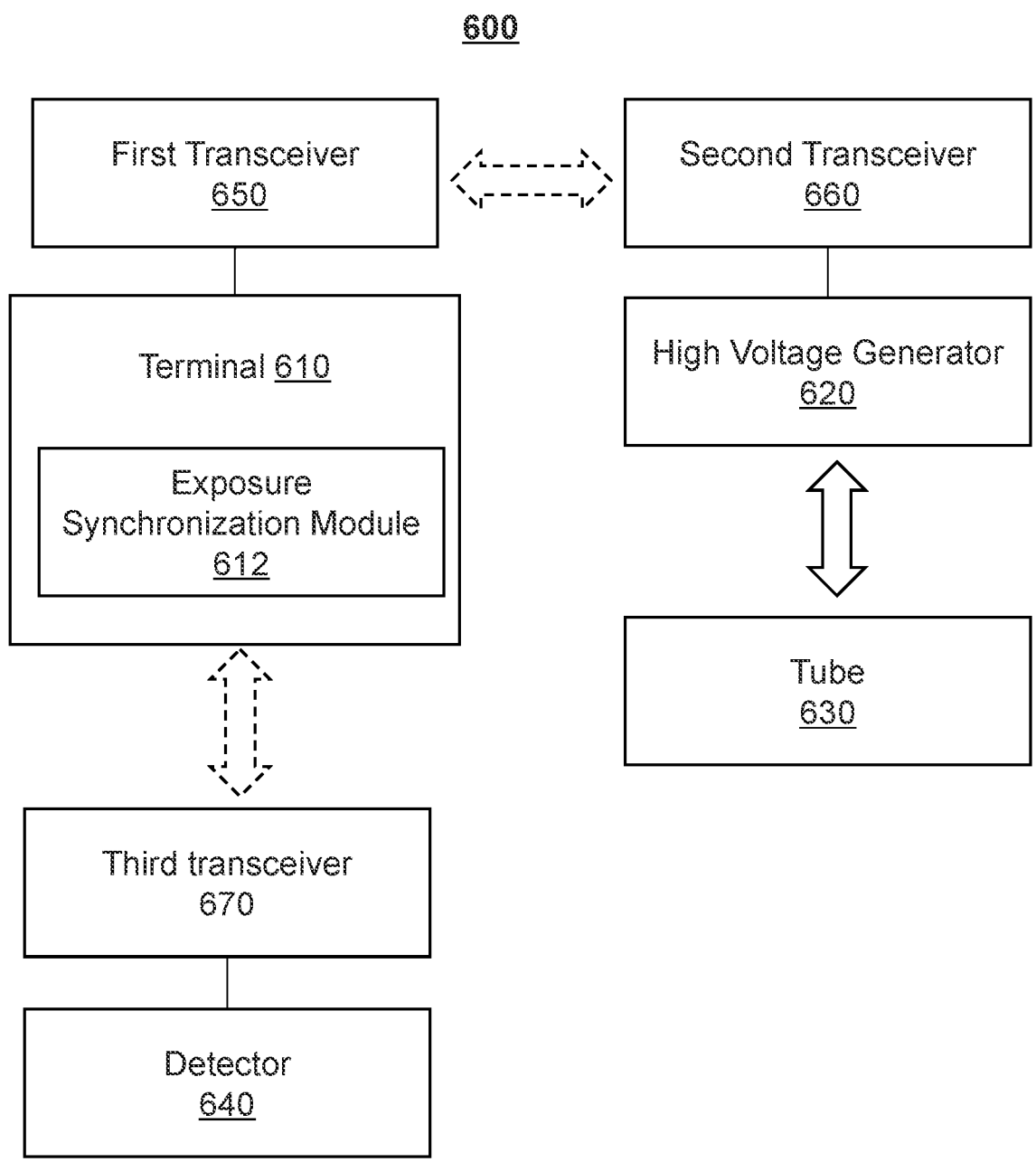
FIG. 6 is a schematic diagram illustrating an exemplary imaging system according to some embodiments of the present disclosure.

FIG. 6 is a schematic diagram illustrating an exemplary imaging system according to some embodiments of the present disclosure. In some embodiments, an imaging system 600 may be an example of the imaging system 100 or a portion of the imaging system 100. As illustrated in FIG. 6, the imaging system 600 may include an imaging device, a terminal 610, an exposure synchronization module 612, a first transceiver 650, a second transceiver 660, and a third transceiver 670. The imaging device may include an X-ray source and a detector 640. The X-ray source may include a high voltage generator 620 and a tube 630.

The terminal 610 may be configured to control the imaging device. In some embodiments, the terminal 610 may transmit a control signal to at least one component of the imaging device to control a status of the at least one component of the imaging device. The control signal may include a readiness signal, an exposure signal, an imaging parameter adjustment signal, or the like, or any combination thereof. The status of the at least one component (e.g., the high voltage generator 620, the tube 630, the detector 640) of the imaging device may include a connection status, a readiness status, power information, temperature information, error information, or the like; or any combination thereof. For example, the terminal 610 may obtain a status of the high voltage generator 620. The terminal 610 may transmit the control signal to the high voltage generator 620 based on the status of the high voltage generator 620. As another example, the terminal 610 may obtain a status of the detector 640. The terminal 610 may transmit the control signal to the detector 640 based on the status of the detector 640.

In some embodiments, the terminal 610 may be the same as or similar to the terminal 140 or the terminal 290. More descriptions of the terminal 610 may be found elsewhere in the present disclosure (e.g., FIG. 1, 2, 3, and descriptions thereof).

The high voltage generator 620 may be configured to generate a high-voltage and current for the tube 630. The tube 630 may include a filament (not shown in FIG. 6) and an anode target (not shown in FIG. 6), The high-voltage generated by the high-voltage generator 620 may trigger the filament to emit a plurality of electrons to form an electron beam. The emitted electron beam may be impinged on a small area on the anode target to generate radiation beams (e.g., X-rays beams) consisting of high-energetic photons. The radiation beams may be collimated by a collimator (not shown in FIG. 6) and project onto a surface of the detector 640. The detector 640 may detect the radiation beams collimated by the collimator and generate data associated with the projection formed by the detected radiation beams (e.g., X-rays beams) as image data (also referred to as projection data). The image data may be transmitted to the terminal 610 for further processing.

The first transceiver 650 may be configured to transmit information of the terminal 610, and receive information from one or more other components (e.g., the high voltage generator 620, the tube 630, the detector 640) of the imaging system 600. For example, the first transceiver 650 may transmit the control signal from the terminal 610 to the one or more other components (e.g., the high voltage generator 620, the tube 630, the detector 640) of the imaging system 600. As another example, the first transceiver 650 may receive statuses of the one or more components (e.g., the high voltage generator 620, the tube 630, the detector 640) of the imaging system 600.

The second transceiver 660 may be configured to transmit information of the high voltage generator 620, and receive information from one or more other components (e.g., the terminal 610, the tube 630, the detector 640) of the imaging system 600. For example, the second transceiver 660 may transmit a status of the high voltage generator 620 to the one or more other components (e.g., the terminal 610, the tube 630, the detector 640) of the imaging system 600. As another example, the second transceiver 660 may receive the control signal from the terminal 610. As still another example, the second transceiver 660 may receive statuses of the one or more other components (e.g., the tube 630, the detector 640) of the imaging system 600.

The third transceiver 670 may be configured to transmit information of the detector 640, and receive information from one or more other components (e.g., the terminal 610, the high voltage generator 620, the tube 630) of the imaging system 600. For example, the third transceiver 670 may transmit a status of the detector 640 to the one or more other components (e.g., the terminal 610, the high voltage generator 620, the tube 630) of the imaging system 600. As another example, the third transceiver 670 may receive the control signal from the terminal 6101. As still another example, the third transceiver 670 may receive statuses of the one or more other components (e.g., the high voltage generator 620, the tube 630) of the imaging system 600.

The exposure synchronization module 612 may be configured to synchronize the high voltage generator 620 and the detector 640 based on the control signal. In some embodiments, the exposure synchronization module 612 may be installed in the terminal 610, as illustrated in FIG. 6. In some embodiments, the exposure synchronization module 612 may be installed in the imaging device. For example, the exposure synchronization module 612 may be operably connected to the high voltage generator 620 and the detector 640. In some embodiments, the exposure synchronization module 612 may be separate from the imaging device and the terminal 610.

In some embodiments, the high voltage generator 620 may receive information (e.g., the control signal) from the terminal 610 and information (e.g., a real-time status of the detector 640) from the detector 640 via the second transceiver 660. The second transceiver 660 may transmit the information of the high voltage generator 620 (e.g., a real-time status of the high voltage generator 620) to the detector 640 via the exposure synchronization module 612. The detector 640 may receive information (e.g., the control signal) from the terminal 610 and information (e.g., the real-time status of the high voltage generator 620) from the high voltage generator 620 via the third transceiver 670. The high voltage generator 620 and the detector 640 may be synchronized based on the control signal. The imaging system 600 may generate image data by imaging the subject based on the control signal and synchronization between the high voltage generator 620 and the detector 640. For example, the terminal 610 may receive readiness signals from the high voltage generator 620 and the detector 640 via the first transceiver 650. The terminal 610 may generate the control signal (e.g., an exposure signal) and process the control signal. The terminal 610 may transmit the processed control signal to the high voltage generator 620. The high voltage generator 620 may transmit the processed control signal to the exposure synchronization module 612. The exposure synchronization module 612 may transmit the processed control signal to the detector 640. The detector 640 may transmit the readiness signal to the exposure synchronization module 612 and the high voltage generator 620. The high voltage generator 620 may generate the high-voltage and current for the tube 630 to generate radiation beams (e.g., X-rays beams).

In some embodiments, the terminal 610, the exposure synchronization module 612, the high voltage generator 620, the tube 630, the detector 640, the first transceiver 650, the second transceiver 660, and the third transceiver 670 may be connected to and/or communicate with each other via a wireless connection, a wired connection, or a combination thereof. The wired connection may include an electrical cable, an optical cable, a telephone wire, or the like, or any combination thereof. The wireless connection may include a Bluetooth™ link, a Wi-Fi™ link, a WiMax™ link, a WLAN link, a ZigBee link, a mobile network link (e.g., 3G, 4G, 5G), or the like, or any combination thereof. The connection between the components of the imaging system 600 may be variable. For example, the terminal 610 may be connected to the high voltage generator 620 wirelessly. As another example, the terminal 610 may be connected to the detector 640 wirelessly. As still another example, the high voltage generator 620 may be connected to the detector 640 wirelessly. As still another example, the high voltage generator 620 may be connected to the tube 630 via a cable.

Compared to an imaging device whose components, such as a high voltage generator, a detector, and a terminal, that are connected to and/or communicate with each other via a wired connection, the imaging device or system according to some embodiments of the present disclosure whose components, such as the high voltage generator 620, the detector 640, and the terminal 610, may be connected to and/or communicate with each other via a wireless connection, which may improve the flexibility and/or availability of mobile imaging.

The imaging system 600 disclosed in the present disclosure may include the imaging device and the terminal 610. The high voltage generator 620 and the detector 640 in the imaging device may be connected to and/or communicate with the terminal 610 via a wireless connection. The terminal 610 may transmit the control signal to the imaging device. The imaging device may generate the image data by imaging the subject based on the control signal and synchronization between the high voltage generator 620 and the detector 640. The terminal 610 may obtain, process, and transmit the image data. Accordingly, the imaging device may be controlled via the terminal 610 and the image data may also be processed via the terminal 610. Due to the wireless communication between the terminal 610 and the imaging device, the terminal 610 may be used away from the imaging device. Therefore, the imaging device does not need to be moved frequently, and the image data may be processed conveniently and quickly, which may improve the flexibility and/or availability of mobile imaging.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the imaging system 600 may include one or more additional components not described, and/or without one or more components illustrated in FIG. 6. For example, the first transceiver 650, the second transceiver 660, and the third transceiver 670 may be omitted.

Figure 7:
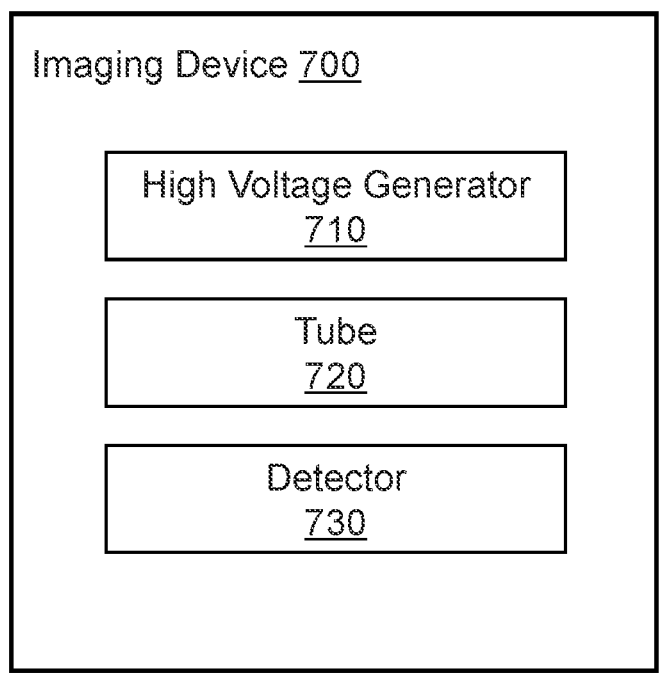
FIG. 7 is a schematic diagram illustrating an exemplary imaging device according to some embodiments of the present disclosure.

FIG. 7 is a schematic diagram illustrating an exemplary imaging device according to some embodiments of the present disclosure. In some embodiments, an imaging device 700 may be an example of the imaging device 110 or a portion of the imaging device 110. As illustrated in FIG. 7, the imaging device 700 may include a high voltage generator 710, a tube 720, and a detector 730.

The high voltage generator 710 may be configured to generate a high-voltage and current for the tube 720. In some embodiments, the high voltage generator 710 may receive a control signal from a terminal (e.g., the terminal 140, the terminal 290) and generate the high-voltage and current for the tube 720 based on the control signal.

The tube 720 may include a filament and an anode target. The high-voltage generated by the high-voltage generator 710 may trigger the filament to emit a plurality of electrons to form an electron beam. The emitted electron beam may be impinged on a small area on the anode target to generate radiation beams (e.g., X-rays beams) consisting of high-energetic photons. The radiation beams may be collimated by a collimator and project onto a surface of the detector 730.

The detector 730 may detect the radiation beams collimated by the collimator and generate data associated with the projection formed by the detected radiation beams (e.g., X-rays beams) as image data (also referred to as projection data). The image data may be in a standard format (e.g., DICOM format). In some embodiments, the detector 730 may transmit the image data to the terminal.

The imaging device 700 disclosed in the present disclosure may be connected to and/or communicate with the terminal via a wireless connection. The imaging device 700 may receive the control signal from the terminal and generate the image data associate with the subject. Accordingly, the imaging device 700 may receive information from the terminal wirelessly to perform a scan on the subject, and the scan may be performed conveniently and quickly, which may improve the flexibility and/or availability of mobile imaging.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
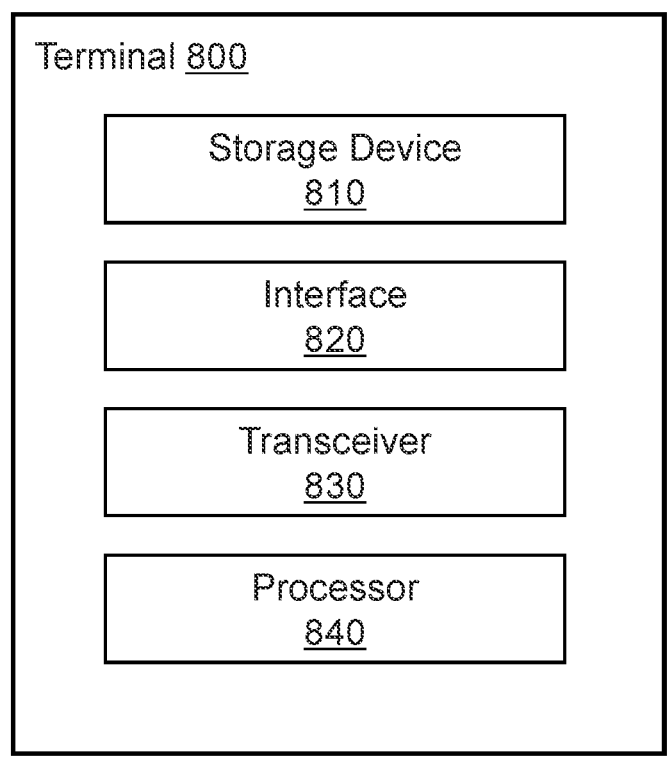
FIG. 8 is a schematic diagram illustrating an exemplary terminal according to some embodiments of the present disclosure.

FIG. 8 is a schematic diagram illustrating an exemplary terminal according to some embodiments of the present disclosure. In some embodiments, a terminal 800 may be an example of the terminal 140 or a portion of the terminal 140. As illustrated in FIG. 8, the terminal 800 may include a storage device 810, an interface 820, a transceiver 830, and a processor 840.

The storage device 810 may be configured to store information/data associated with the imaging system 100, For example, the storage device 810 may store information associated with a subject. As another example, the storage device 810 may store an imaging parameter associated with at least one component of the imaging system 100. As still another example, the storage device 810 may store at least one imaging protocol. As still another example, the storage device 810 may store a status of at least one component of the imaging system 100.

The interface 820 may be configured to generate and/or display information/data associated with the imaging system 100. In some embodiments, the interface 820 may be configured to display information/data associated with the imaging system 100. For example, the interface 820 may display image data associated with a subject. As another example, the interface 820 may display an imaging parameter. As still another example, the interface 820 may display a status of at least one component of the imaging system 100. In some embodiments, the interface 820 may be configured to generate information/data associated with the imaging system 100. For example, the interface 820 may generate a control signal based on a selected imaging protocol from at least one imaging protocol stored in a storage device (e.g., the storage device 810, the storage device 130) of the imaging system 100.

The transceiver 830 may be configured to receive information/data from or transmit information/data to one or more components of the imaging system 100. For example, the transceiver 830 may transmit a control signal to an imaging device (e.g., the imaging device 110). As another example, the transceiver 830 may obtain image data associated with a subject from an imaging device (e.g., the imaging device 110).

The processor 840 may be configured to process information/data associated with the imaging system 100. In some embodiments, the processor 840 may process image data collected by an imaging device (e.g., the imaging device 110). For example, the processor 840 may perform an image segmentation operation, an image classification operation, an image recognition operation, an image registration operation, an image fusion operation, an image binarization operation, an image scaling operation, an image rotation operation, an image cropping operation, a window width and/or window level adjustment operation, a brightness adjustment operation, a grayscale adjustment operation, a histogram operation, or the like, on the image data.

The terminal 800 disclosed in the present disclosure may be connected to and/or communicate with the imaging device (e.g., the imaging device 110) via a wireless connection. The terminal 800 may transmit a control signal to the imaging device and obtain image data from the imaging device. The terminal 800 may be removably attached to the imaging device, and the operation of the terminal may be convenient and simple. When the imaging device is abnormally powered down or a scan of the subject is emergency stopped, an operating system of the terminal 800 may not be damaged and the image data may not be lost. In addition, when the user processes the image data via the terminal 800, the imaging device does not need to be moved, and the image data may be processed conveniently and quickly, which may improve the flexibility and/or availability of mobile imaging.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the terminal 800 may include one or more additional components not described, and/or without one or more components illustrated in FIG. 8. For example, the terminal 800 may further include a network card, a communication interface, a power interface, and/or a memory.

Figure 9:
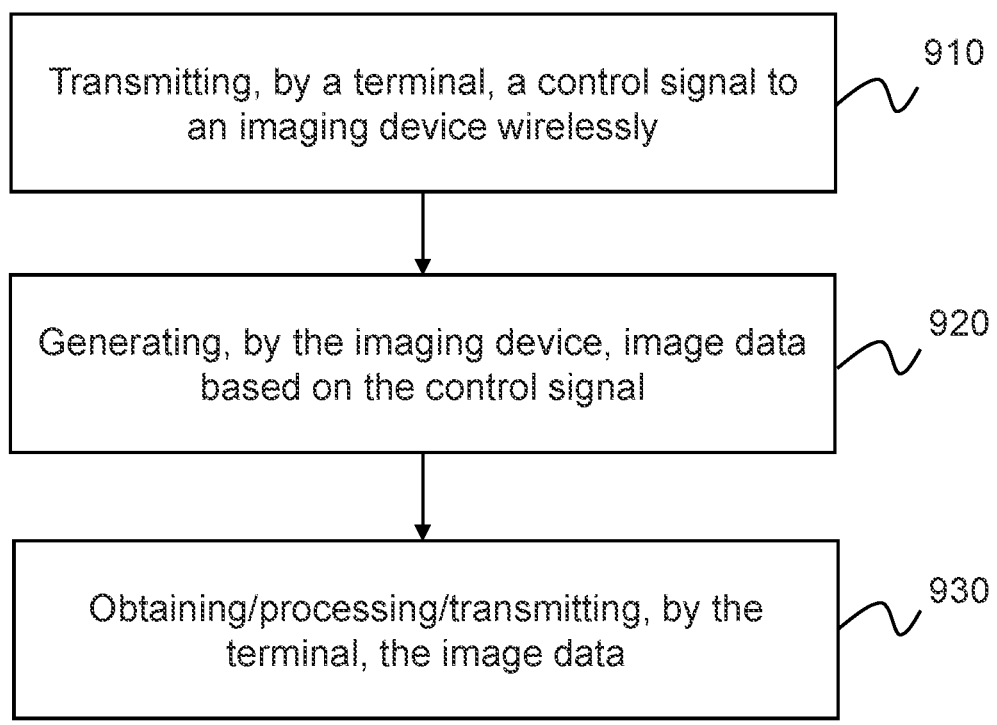
FIG. 9 is a flowchart illustrating an exemplary process for obtaining image data according to some embodiments of the present disclosure.

FIG. 9 is a flowchart illustrating an exemplary process for obtaining image data according to some embodiments of the present disclosure. In some embodiments, the process 900 may be implemented in the imaging system 100 illustrated in FIG. 1. For example, the process 900 may be stored in the storage device 130 and/or the storage (e.g., the storage 420, the storage 590, the storage device 810) as a form of instructions, and invoked and/or executed by the processing device 120 (e.g., the processor 410 of the computing device 400 as illustrated in FIG. 4, the CPU 540 of the mobile device 500 as illustrated in FIG. 5).

In 910, a terminal (e.g., the terminal 140) may transmit a control signal to an imaging device (e.g., the imaging device 110) wirelessly. In some embodiments, the terminal may transmit the control signal to the imaging device via the network 150.

In some embodiments, the terminal may transmit the control signal to at least one component (e.g., a high voltage generator, a detector, a tube) of the imaging device to control a status of the at least one component of the imaging device. The control signal may include a readiness signal, an exposure signal, an imaging parameter adjustment signal, or the like, or any combination thereof. The status of the at least one component of the imaging device may include a connection status, a readiness status, power information, temperature information, error information, or the Ike, or any combination thereof. For example, the terminal may transmit the control signal to the high voltage generator and/or the detector based on a status of the high voltage generator and/or a status of the detector.

In some embodiments, an exposure synchronization module (e.g., the exposure synchronization module 612) may perform a synchronization operation on the high voltage generator and the detector based on the control signal. For example, the terminal may receive readiness signals from the high voltage generator and the detector. The terminal may generate the control signal (e.g., an exposure signal) based on the readiness signals received from the high voltage generator and the detector. The terminal may transmit the control signal to the high voltage generator. The high voltage generator may transmit the control signal to the exposure synchronization module. The exposure synchronization module may transmit the control signal to the detector. The detector may transmit the readiness signal to the exposure synchronization module and the high voltage generator. Accordingly, the high voltage generator and the detector may be synchronized based on the control signal.

In 920, the imaging device (e.g., the imaging device 110) may generate image data based on the control signal.

In some embodiments, the imaging device may generate the image data based on the control signal and the synchronization between the high voltage generator and the detector. For example, after the synchronization between the high voltage generator and the detector is completed, the high voltage generator may generate a high-voltage and current for the tube. The tube may generate radiation beams (e.g., X-rays beams) consisting of high-energetic photons. The detector may detect the radiation beams and generate data associated with the projection formed by the detected radiation beams (e.g., X-rays beams) as the image data.

In 930, the terminal (e.g., the terminal 140) may obtain/process/transmit the image data. In some embodiments, the terminal may obtain the image data from the imaging device via the network 150. The terminal may transmit the image data to one or more other components of the imaging system 100 via the network 150.

In some embodiments, the terminal may process the image data. For example, the terminal may perform an image segmentation operation, an image classification operation, an image recognition operation, an image registration operation, an image fusion operation, an image binarization operation, or the like, on the image data.

The method disclosed in the present disclosure may be applicable to a medical imaging system. The medical imaging system may include an imaging device (e.g., an X-ray imaging device) and a terminal. The imaging device may be connected to and/or communicate with the terminal via a wireless connection. The imaging device may generate image data by imaging a subject based on a control signal. The imaging device may transmit a status of at least one component of the imaging device to the terminal for display. The imaging device may transmit the image data to the terminal for display and/or processing. The terminal may transmit the control signal. The terminal may display the status of the at least one component of the imaging device. The terminal may obtain/process/transmit the image data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, an exposure synchronization operation may be added before operation 920. The exposure synchronization module may synchronize the high voltage generator and the detector of the imaging device based on the control signal.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A system, comprising:
   an imaging device configured to image a subject;
   a voice processing device configured to receive a first voice signal from or transmit a second voice signal to the subject when the subject is positioned within the imaging device; and
   a terminal configured to receive a third voice signal from or transmit a fourth voice signal to a user.

2. The system of claim 1, further comprising:
   an image capture device configured to capture an image representing a status of the subject when the subject is positioned within the imaging device.

3. The system of claim 1, further comprising:
   a storage device, in communication with the terminal, configured to store information including or relating to at least one of the first voice signal, the second voice signal, the third voice signal, the fourth voice signal, or a recorded voice signal, wherein
   the terminal is configured to transmit at least a portion of the information stored in the storage device to at least one of the subject or the user.

4. The system of claim 1, wherein the voice processing device includes at least one of a speaker, a microphone, or an integrated device including the speaker and the microphone.

5. The system of claim 1, wherein the terminal includes a second voice processing device.

6. The system of claim 5, wherein the second voice processing device includes at least one of a speaker, a microphone, or an integrated device including the speaker and the microphone.

7. The system of claim 1, wherein the terminal is configured to receive an instruction provided by the user for controlling the imaging of the subject by the imaging device.

8. The system of claim 1, wherein the terminal includes an exposure control unit, the exposure control unit being configured to adjust an exposure parameter and transmit a command for adjusting the exposure parameter to the imaging device.

9. The system of claim 1, wherein the terminal includes a movement control unit, the movement control unit being configured to transmit to the imaging device a second command for controlling a movement of at least one component of the imaging device.

10. The system of claim 1, wherein the terminal is removably attached to the imaging device.

11. The system of claim 1, wherein the terminal is a portable tablet.

12. The system of claim 1, wherein the imaging device is an X-ray imaging device.

13. The system of claim 1, wherein
    the imaging device includes:
       an X-ray source including a high voltage generator and a tube; and
       a detector,
    the terminal is in communication with the high voltage generator and the tube to transmit a control signal,
    the system further includes:
       an exposure synchronization module configured to synchronize the high voltage generator and the detector based on the control signal,
    the imaging device is configured to generate image data by imaging the subject based on the control signal and synchronization between the high voltage generator and the detector, and
    the terminal is configured to obtain, process, and transmit the image data.

14. The system of claim 13, further comprising:
    a first transceiver, wherein the first transceiver is configured to transmit the control signal and receive second information from at least one of the high voltage generator or the tube;
    a second transceiver, wherein the second transceiver is configured to transmit third information of the high voltage generator, and receive fourth information from at least one of the terminal or the tube; and
    a third transceiver, wherein the third transceiver is configured to transmit fifth information of the detector, and receive sixth information from at least one of the terminal or the high voltage generator.

15. The system of claim 13, wherein the terminal is further configured to obtain a status of at least one of the high voltage generator or the detector.

16. The system of claim 1, wherein communication between at least two of the imaging device, the voice processing device, or the terminal is wireless.

17. The system of claim 1, further comprising:
    a picture archiving and communication system (PACS), wherein:
    at least one of the imaging device, or the terminal is further configured to communicate with the PACS.

18. The system of claim 1, wherein the voice processing device is mounted on the imaging device.

19. The system of claim 2, wherein the image capture device is mounted on the imaging device.

* * * * *